United States Patent [19]
Capuano et al.

[11] Patent Number: 5,879,629
[45] Date of Patent: Mar. 9, 1999

[54] PROCESS FLOW INJECTION ANALYZER AND METHOD

[75] Inventors: Italo A. Capuano, Orange; William T. Lefebvre, Rocky Hill; Kenneth E. Creasy, Wallingford, all of Conn.

[73] Assignee: Olin Corporation, Cheshire, Conn.

[21] Appl. No.: 723,655

[22] Filed: Oct. 3, 1996

Related U.S. Application Data

[62] Division of Ser. No. 376,711, Jan. 23, 1995, Pat. No. 5,604,132.

[51] Int. Cl.⁶ .................................................. G01N 35/08
[52] U.S. Cl. .......................... 422/82; 422/81; 422/82.05; 422/82.09; 436/52; 436/139; 436/164; 436/166; 436/171; 436/180; 250/339.07; 250/339.08; 250/339.12
[58] Field of Search .................................. 422/82, 82.05, 422/68.1, 81, 82.09; 436/52, 53, 164, 166, 174, 171, 179, 139, 180; 250/435, 339.07, 339.08, 339.12

[56] References Cited

U.S. PATENT DOCUMENTS

| | | | |
|---|---|---|---|
| 3,871,826 | 3/1975 | Bakay | 436/180 |
| 4,283,201 | 8/1981 | DeFord et al. | 422/62 |
| 4,315,754 | 2/1982 | Ruzicka et al. | 422/81 |
| 4,960,711 | 10/1990 | Aoki et al. | 436/124 |
| 5,019,515 | 5/1991 | Gisin et al. | 436/52 |
| 5,080,866 | 1/1992 | Petty et al. | 422/80 |
| 5,212,095 | 5/1993 | Miki et al. | 436/52 |
| 5,217,590 | 6/1993 | Lauer et al. | 204/180.1 |
| 5,444,807 | 8/1995 | Liu | 382/125 |
| 5,599,503 | 2/1997 | Manz et al. | 422/82.05 |

OTHER PUBLICATIONS

Garrigues et al., "FIA–FT–IR Determination of Ibuprofen in Pharmaceuticals", Talanta, vol. 40, No. 1, pp. 89–93, 1993.

*Primary Examiner*—Long V. Le
*Attorney, Agent, or Firm*—Wiggin & Dana; Dale L. Carlson; Thomas F. Presson

[57] ABSTRACT

A method and analyzer for monitoring the progress of a chemical process in which a fixed volume sample of the reactive mixture of the chemical process is periodically gathered and injected into a fluid stream of a liquid carrier. The sample in the liquid carrier is passed through an infrared detector which detects the amount present in the sample of a species of the reaction mixture which is indicative of the progress of the chemical process.

9 Claims, 1 Drawing Sheet

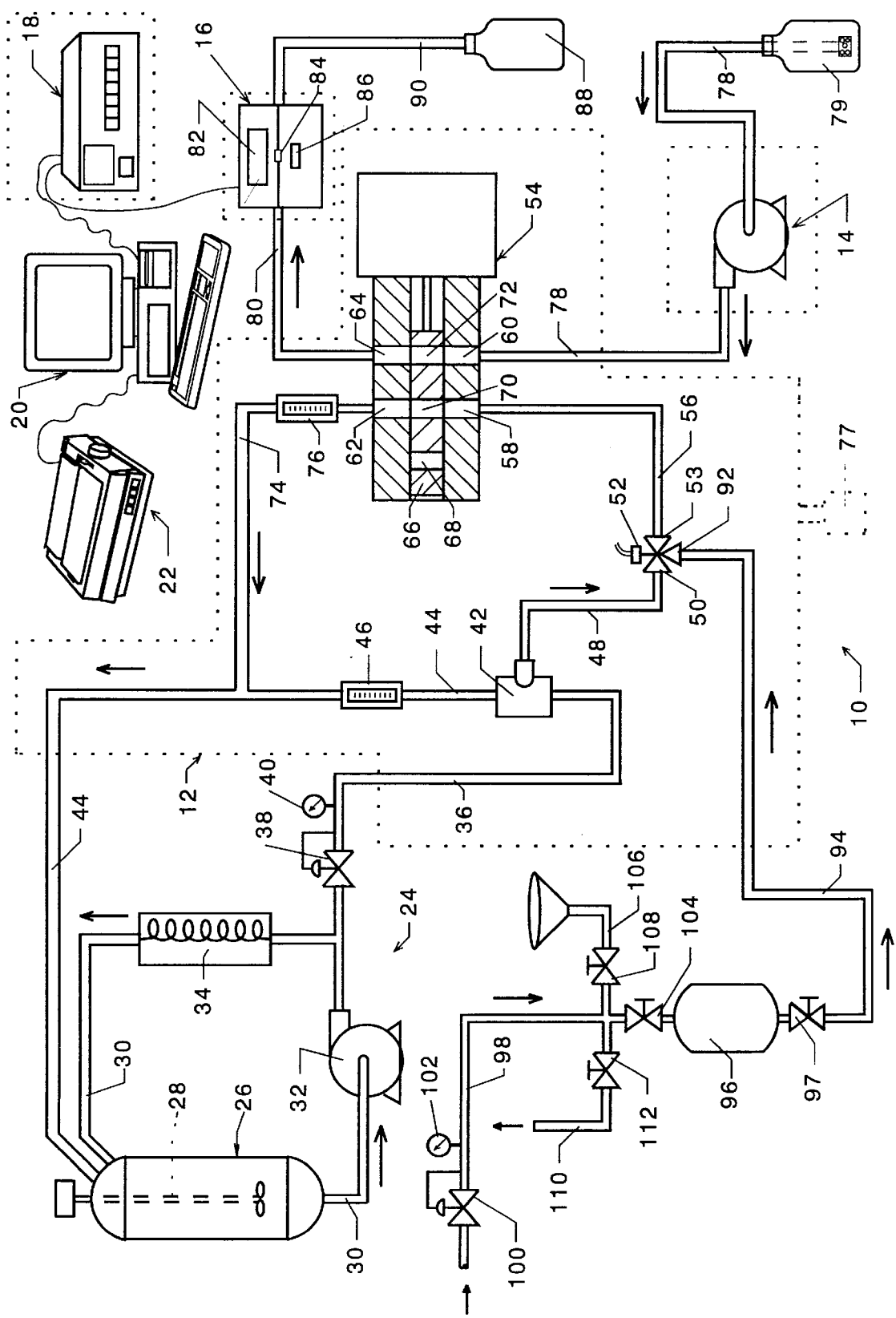

PROCESS FLOW INJECTION ANALYZER AND METHOD

This is a division of application Ser. No. 08/376,711, filed on Jan. 23, 1995, now U.S. Pat. No. 5,604,132 and which is incorporated herein by reference in its entirety.

BACKGROUND OF INVENTION

Field of the Invention

This invention relates generally to a method and analyzer for monitoring a chemical process. More particularly, this invention relates to a method and analyzer for monitoring the progression of a chemical reaction occurring in a chemical process using process flow injection analysis.

Background

In some chemical processes, particularly batch processes, it is necessary that the particular chemical reaction be terminated at a given point in time, either because the desired properties of the reaction product have been reached and further processing will diminish the desired properties, or the reaction itself could become uncontrollable or reach an unsafe condition. This may be particularly true in process involving the conversion of monomers to polymers where the specific properties of the resultant product are dependant upon the extent of polymerization.

It is thus desirable that the progress of such reactions be monitored at frequent intervals and with a great deal of accuracy so that the reaction may be timely controlled and also so that an operator will be aware of when the reaction has reached its desired limit and the necessary steps can be taken to quench or otherwise terminate the reaction.

Also, in some chemical processes, the reaction is initiated and sustained by adding a catalyst and stopped by adding a quenching agent. In such cases, it is desirable that the process be closely monitored so that the supply of the catalyst and addition of the quenching agent may be timely controlled.

Attempts to monitor such reactions by analyzing the reaction solution using known methods such as Fourier Transform infrared spectroscopy (FTIR) have not been successful. Due to the strong absorption of infrared radiation by the materials involved, FTIR analysis can only be performed using attenuated total reflectance (ATR) flow cells, which reduces absorption without effecting spectral resolution. However, the optical surfaces of the cells used to analyze a particular species of a given polymerization process can become coated with a film of polymer species which blocks the transmission of the light thus interfering with the analysis. While numerous solvent cleaning schemes have been tried to remove the coating between each series of analyses, the films appeared irreversibly coated on the optical crystals of the flow cells and only physically wiping the delicate crystals removed the coatings.

SUMMARY OF THE INVENTION

In view of the above, it is an object of the present invention to provide an improved method and analyzer for monitoring a chemical process.

It is a more specific object of the present invention to provide a method and analyzer for monitoring a chemical reaction occurring in a chemical process which detects the amount of a particular species present in the reaction mixture which is indicative of the progress of the reaction.

It is a further object of the present invention to provide a method and analyzer for monitoring a chemical reaction occurring in a chemical process using process flow injection analysis.

It is yet another object of the present invention to provide a method and analyzer for monitoring the chemical reaction occurring in a chemical process which can be used on-site and on a continuous basis.

Yet another object of the present invention is the provision of a method and apparatus for monitoring a chemical reaction occurring in a chemical process which will operate reliably and without service or maintenance for relatively long periods of time.

These and other objects and advantages may be achieved in accordance with the present invention through a method for monitoring a chemical reaction in a chemical process which comprises gathering a sample of the reaction mixture of the chemical process, injecting the gathered sample into a flow stream of a dry organic liquid carrier, and passing said flow stream of said liquid carrier containing the sample through an infrared detector to detect the amount of a species of the reaction mixture which is indicative of the progress of the chemical process.

An analyzer for monitoring a chemical reaction in a chemical process in accordance with the present invention comprises a sample gatherer for gathering a sample of the reaction mixture of the chemical process, a source of a dry organic liquid carrier, an injector for injecting the sample into a flow stream of said dry organic liquid carrier, an infrared detector for detecting the amount of a particular species of the reaction mixture which is indicative of the progress of the chemical process, and means for passing said flow stream of the liquid carrier with said sample through said infrared detector.

BRIEF DESCRIPTION OF THE DRAWINGS

The objects and advantages of the present invention will become more apparent by reference to the following detailed description and to the accompanying drawing in which:

The Figure is a schematic diagram of an analyzer constructed in accordance with the present invention.

DETAILED DESCRIPTION

The Figure of the drawing shows a schematic diagram of an analyzer according to the present invention which is capable of monitoring a chemical reaction by detecting a change in some physical property that occurs during the chemical reaction. For example, the concentration or quantity of a particular chemical species produced during the reaction and which is indicative of the progress of the reaction may be detected.

As an example, the apparatus and method of the present invention may be used in the monitoring of the process involving the production of polyvinyl acetate from vinyl acetate by measuring the absorption band at 3.5 microns due to the vinyl acetate monomer and noting its decrease. As another example, in the process of making polypropylene glycol from propylene glycol and propylene oxide, the process may be monitored by measuring the absorption band at 12 microns due to the propylene oxide monomer and noting its decrease. Other examples include the monitoring of the production of acetic acid from ethyl alcohol by measuring the absorption band at 5.9 microns due to the carbonyl group of the acetic acid product and noting its increase, and the monitoring of the production of monochlorobenzene from benzene and chlorine by measuring the absorption band at 13.5 microns due to the C—Cl (carbon-chlorine) group of the monochlorobenzene product and noting its increase.

Referring to the drawing, the analyzer 10 of the present invention may generally comprise a sampling unit 12, a carrier pump 14, an infrared detector 16 and a microprocessor or controller 18. Each of these components may be provided as a separate module as indicated by the broken lines contained in its own housing and mounted in a cabinet or on a common frame (not shown). A host computer 20 and output unit 22 such as a printer or plotter, may be linked to the controller 18, but provided at a remote location such as in a control room.

The chemical reaction to be monitored may be performed with standard process equipment 24. By way of example, such process equipment may include a reactor vessel 26 having a mixer 28 associated therewith to stir the ingredients. A recirculating line 30 may be provided which contains a pump 32 and a heat exchanger 34 as shown in the drawing. The heat exchanger 34 serves to cool the recirculating reaction mixture to maintain the desired temperature in the reactor vessel 26 as the reaction progresses.

The sampling unit 12 is connected to the process equipment 24 by a reaction mixture infeed line 36 which is attached at its downstream end to the recirculating line 30 of the process equipment between the pump 32 and heat exchanger 34. Although the reaction mixture infeed line 36 is shown connected to the recirculating line 30, depending upon the particular process and the equipment being used, the infeed line 36 may be connected to the process equipment at any convenient location which will provide a source of the liquid reaction mixture. The reaction mixture infeed line 36 has a pressure regulator 38 therein to maintain the pressure of the incoming reactive sample at a constant pressure. A pressure gauge 40 may be mounted in the line 36, downstream of the pressure regulator 38 to provide an indication of the pressure of the reactive sample in line 36.

The downstream end of the reaction mixture infeed line 36 is connected to a filter 42. A return line 44, having a flow meter 46 therein as shown, connects the filter 42 to the reactor vessel 26 whereby a relatively large portion of the reaction mixture from the filter 42 is transported back to the reactor vessel 26. A portion of the reaction mixture from the reaction mixture infeed line 36 exits the filter 42 through a filter outlet line 48 connected at one end to the filter 42 and at the other end to an inlet port 50 of a three-way valve 52. The filter 42 may be of any suitable type capable of preventing solid components from passing into the filter output line 48, and may be similar to a wire strainer of an appropriate mesh.

An outlet port 53 of the three-way valve 52 is connected to a sampling valve 54 by a reaction mixture sample input line 56. The sampling valve 54 has four ports 58, 60, 62 and 64 as indicated in the drawing. Two of the ports 58 and 60 are inlets and two of the ports 62 and 64 are outlets. The inlet port 58 is coaxial with outlet port 62 forming a first inlet and outlet set, and inlet port 60 is coaxial with outlet port 64 forming a second inlet and outlet set. The sampling valve 54 includes a moveable slider 66 positioned between the inlet ports 58,60 and the outlet ports 62,64 as shown in the drawing. The slider 66 includes three orifices, 68, 70 and 72 extending therethrough which are adapted to be aligned with the inlet and outlet sets to provide communication between the inlet and outlet ports of each set when the slider 66 is moved between its two positions upon actuation of the valve 54. The middle orifice 70 is the sampling gathering orifice and is of a predetermined size such that a plug of known volume of the reaction mixture will be contained therein.

The sampling valve 54 is an electrically operated valve such as a solenoid actuated, pneumatically operated valve in which the slider 66 is moveable between two positions, a first, or non-sampling, position and a second,or sampling, position. The valve 54 is controlled by the microprocessor 18 which provides an appropriate signal at timed intervals to move the slider 66 of the valve 54 between the first and second positions.

In the first, or non-sampling, position of the sampling valve 54, which is the position shown in the drawing, the middle or sampling orifice 70 of the slider 66 is positioned so that it is coaxial with the inlet port 58 and the outlet port 62 providing communication within the valve between these two ports. Also, in the first, or non-sampling, position of the valve, the orifice 72 in the slider 66 is positioned so that it is coaxial with the inlet port 60 and the outlet port 64 to provide communication within the valve between these two ports. In the first, or non-sampling, position of the valve, the orifice 68 is, in effect, inactive.

When the sampling valve 54 is actuated into its second, or sampling, position, the slider 66 is moved to the right from its position shown in the drawing and the middle or sampling orifice 70 of the slider 66 is moved into alignment with the inlet port 60 and outlet port 64, while the orifice 68 is moved into alignment with the inlet port 58 and the outlet port 62, providing communication between those two ports. In the second position, the orifice 72 is inactive.

The reaction mixture input line 56 from the filter 42 is connected to the inlet port 58 of the sampling valve 54. A sample return line 74 is connected at one end to the outlet port 62 of the sampling valve 54 which is coaxial with the inlet port 58. The other end of the sample return line 74 is connected to the filter return line 44 from the filter 42 to the reaction vessel 26 at a point upstream of the flow meter 46. A flow meter 76 may be positioned in the sample return line 74 as shown. This arrangement provides a path for the reaction mixture sample from the filter 42 through the three-way valve 52, through the sampling valve 54 and back to the reactor vessel 26 though return lines 74 and 44 when the sampling valve 54 is in its first position.

The sampling unit 12, including the filter 42, the three-way valve 52, the sampling valve 54 and the associated flow lines are maintained at a constant temperature by a heater 77 to help ensure the analytical accuracy of the measurement. The heater 77 may be a forced hot air heater although other types of heaters such an electrical radiation heater may be used.

The second inlet port 60 of the sampling valve 54 is connected to a source of carrier fluid by means of a carrier fluid input line 78. The carrier fluid is a dry (non-aqueous) organic liquid, and one in which the reaction mixture is soluble and one that doesn't absorb the infrared light in the range of wavelengths being used for detecting the desired species of the reaction mixture. The carrier fluid, in the case of the production of polyvinyl acetate from vinyl acetate, may be toluene stored in an appropriate container 79. Example of other carrier fluids which may be used depending upon the process include acetonitrile, methanol and xylene.

The carrier fluid may also contain a quenching agent to quench the reaction of the reaction mixture, helping to increase the accuracy of the detection procedure. An acid, such as hydrochloric acid, is one example of a quenching agent and may be used, for instance, in the case of the monitoring of the polymerization of propylene glycol to polypropylene glycol, which uses a base catalyst. In cases where the polymerization reaction uses an acid catalyst, the quenching agent may be a base such as sodium hydroxide.

The carrier pump 14 is provided in the carrier fluid input line 78 to provide a high degree of control of the carrier flow rate to ensure precise resident times of the reactive mixture samples in the detector 16 and control the dispersion of the reaction mixture in the carrier fluid. For this purpose, the pump 14 is of the type commonly used for high performance liquid chromatography such as an isocratic pump. Such pumps are commercially available. A specific example of a suitable pump is an IsoCrom isocratic pump manufactured by Spectra-Physics, Inc. which is available as a discrete unit and may be housed in the instrument frame or cabinet separate from the other components.

The outlet 64 of the sampling valve 54, which is coaxial with the inlet port 60, has one end of a sample feed tube 80 connected thereto. The other end of the sample feed tube 80 is connected to the detector 16. The flow of the carrier fluid through the tubing 80 to the infrared detector 16 effects the dispersion of the plug of the reaction mixture sample in the carrier fluid stream. At low flow rates there is more diffusion of the sample plug in the carrier fluid and at high rates there is less diffusion, but more turbulent mixing of the reaction mixture plug in the carrier fluid stream. While both diffusion and turbulent mixing tend to interfere with the analysis by causing dilution of the sample in the carrier stream, the ideal characteristic is to have laminar flow in the tubing 80 leading from the sample valve 54 to the infrared detector 16, and the length of the tubing 80 as short as possible and the diameter of the tubing relatively small. For example, the diameter of the tubing 80 may be 1/16" and its length 6" or less.

The infrared detector 16 is preferably one which operates in the mid-infrared range, i.e. a range of about 2.5 to about 14 microns. Such infrared detectors are readily available on a commercial basis. The commercial infrared detectors generally include an infrared source 82, a flow cell 84 through which the sample passes, and an infrared sensor 86 which measures the voltage produced at a thermocouple by the infrared radiation passing through the cell 84 and reaching the thermocouple surface. The infrared source 82 provides an infrared light which is directed through the cell 84 and is partially absorbed in the cell by the chemical species of the reaction mixture which is selected to be detected. The infrared radiation passing through the cell 84 and reaching the sensor 86, heats the sensor surface and produces a voltage signal indicative of the amount of infrared radiation absorbed. The amount of radiation absorbed is proportional to the amount of the selected chemical species present in the sample in the flow cell 84. Thus, the signal produced by the sensor 86 is indicative of the amount of the selected chemical species present in the sample. An example of one suitable commercial detector is the MIRAN®-1A General Purpose Infrared Analyzer manufactured by the Foxboro Company.

After passing through the detector 16, the carrier fluid, along with any sample of the reaction mixture entrained therein passes to a waste collection receptacle 88 through a waste line 90 which extends between the detector 16 and the receptacle 88.

The signal from the detector 16 is processed by the microprocessor 18 and computer 20 to provide a concentration profile of the chemical species being detected. The computer 20 may be programmed to calculate the rate of progress of the reaction and display the progress, in terms of concentration of the desired ingredient, on the monitor of the computer 20 and also on the attached printer 22. The monitor of the computer 20 may also provide a display showing the concentration profile of the most recent sample, the trend tracking the progress of the reaction, and also any alarms encountered by the instrumentation.

A supply of a standard solution is connected to the second inlet port 92 of the three-way valve 52 by a standard solution feed line 94. The standard solution may be stored in any suitable type of container 96 which is connected to the standard solution feed line 94 through a shut-off valve 97. A source of a pressurized gas is connected to the container 96 by an incoming pressurized gas line 98 having one end connected to a suitable source of inert gas or air under pressure and the other end connected to the container 96. This pressurized gas provides a force to move the standard solution through the system. A suitable gas for this purpose is preferably any inert gas or air which is readily available on-site and thus requires no additional equipment or servicing such as would be required by separate supply tanks that must be changed. Examples of a suitable gas for use as the standard solution carrier are nitrogen and purified air.

The incoming pressurized gas line 98 has a pressure regulator 100 therein to maintain a constant pressure of the gas being supplied to the container 96. A pressure gauge 102 may also be provided in the gas line 98 downstream of the pressure regulator 100 to provide an indication of the pressure of the incoming gas. A shutoff valve 104 is provided in the incoming inert gas line 98 immediately before its connection to the storage container 96. A solution fill line 106 having a shutoff valve 108 therein connects with the incoming inert gas line 98 immediately upstream of the shut-off valve 104. The shutoff valve 108 is provided in the solution fill line 106 downstream of its connection to the incoming inert gas line 98. A vent line 110 is also connected to the incoming inert gas line 98 immediately upstream of the shutoff valve 104 and has a shut off valve 112 therein.

The standard solution storage container 96 may be filled by opening all three shutoff valves 104, 108 and 112 and feeding an appropriate solution into the solution infeed line 106. When the desired amount of standard solution is present in the storage container 96, the supply to the fill line may be discontinued and the shutoff valves 108 and 112 closed. The standard solution may be a reaction mixture that has been taken from the reaction vessel 26 and analyzed in the laboratory to ascertain the exact composition or concentration of the component which is to be detected in the infrared detector 16, or, for example, be a solution made up in the laboratory. This standard solution may be fed to the infrared detector 16 through the three-way valve 52 and sampling valve 54 at appropriate times to calibrate the instrumentation and validate analyses. The three-way valve 52 may be any type of an electrically actuated valve such as a solenoid actuated valve which can be controlled by the microprocessor 18.

In operation, a supply of the reaction mixture from the reactor vessel 26 is continuously fed from the recirculating line 30 through the pressure regulator 38 and filter 42 to the three-way valve 52. The three-way valve 52 is normally positioned so that the reaction mixture will flow through the three-way valve 52 from the filter 42 to the sampling valve 54 except when it is desired to feed the standard solution to the sampling valve 54 or detector 16 as will be explained below.

With the sampling valve 54 in its first, or non-sampling, position, the reaction mixture flows into the inlet port 58 of the sampling valve 54, through the middle or sampling orifice 70 of the slider 66 which has a fixed volume, and out through the outlet port 62 of the sampling valve 54. The reaction mixture then flows through the return line 74 to the filter return line 44 and back into the reactor vessel 26. At the same time, with the sampling valve 54 in its first, or non-sampling, position, the liquid carrier continuously flows from its storage container 79 under pressure from the isocratic pump 14 through the liquid carrier input line 78 to the inlet port 60 of the sampling valve 54. The carrier fluid flows through the orifice 72 in the slider 66 of the sampling valve 54 out through the outlet port 64 into the sample feed line 80 to the infrared detector 16. The carrier fluid then flows from the detector 16 through the outlet line 90 into the liquid waste container 88.

When it is desired to take a sample, at timed intervals as programmed by the controller 18, the sampling valve 54 is actuated by a signal from the microprocessor 18 to move it into its second or sampling position. In such position, the slider is moved into its right-most position so that the middle or sampling orifice 70, containing a plug of reaction mixture of a predetermined volume, is aligned with the ports 60 and 64. In this position, the carrier fluid entering the inlet port 60 sweeps through the valve 54 pushing the plug of reaction mixture from the orifice 70 out through the outlet port 64 to the detector 16. The reaction sample entrained in the carrier fluid stream then passes through the flow cell of the infrared detector wherein the chemical species of the reaction mixture which absorbs the specific wavelength of the infrared light will be detected and a signal generated as described above.

The standard solution may be used to calibrate the system when desired. When calibrating the system, the standard solution is first used to flush the reaction mixture from the sampling valve 54 prior to the injection of a sample of the standard solution into the liquid carrier flow stream. When calibration is desired, before the sampling valve is moved into its second, or sampling position, the three-way valve 52 is actuated to temporarily shut-off the supply of the reaction mixture to the sampling valve 54 and permit the standard solution from the storage container 96 to flow through the three-way valve 52 to the inlet port 58 of the sampling valve 54 through the line 56. The standard solution then passes through the sampling orifice 70 in the slider 66 of the sampling valve 54 and out the outlet port 62 into the return line 74, thereby flushing any of the old reaction mixture from the orifice 70.

After an appropriate period of time to accomplish the flushing of the old reaction mixture from the sampling orifice 70 of the sampling valve 54, the sampling valve 54 may be actuated by a signal from the microprocessor 18 to move it into its second, or sampling position, which moves the sampling orifice 70 into alignment with the ports 60 and 64 so that a plug of the standard solution will be carried by the liquid carrier from the sampling orifice 70 through the outlet port 64 of the sampling valve 54 through line 80 to the detector 16.

When the plug of the standard solution has passed through the detector 16, the three-way valve 52 may be actuated to shut-off the flow of standard solution to the sampling valve 54 and the sampling valve 54 returned to its first position to permit the reaction mixture from the reactor 26 to flow again to the sampling valve 54 and through the sampling orifice 70.

By way of example, the sampling unit 12 may be housed in two units, one containing the flow meters 46 and 48 and the other containing the sampling valve 54. Both of the units may be thermostated by using a hot air heater as indicated schematically by the reference numeral 77. The flow lines inside the units may be separately heated using heating tape with temperature control provided by a variable resistor transformer. All areas where the reaction mixture is flowing should be maintained at a constant temperature suitable for the particular application to ensure analytical accuracy.

In the monitoring of the process of the production of acetic acid from ethyl alcohol, the operating parameters of the sampling unit may be such that the reaction mixture flow through the sampling valve 54 as measured by the flowmeter 76 is between 60 and 80 milliliters per minute (mL/min). The reactive mixture flow from the filter 54 back to the reactor vessel 26 through the return line 44 as measured by the flowmeter 46 may be between 5 and 10 gallons per hour (G.P.H.). The temperature of the sampling unit may be maintained about 45° C. The microprocessor may be set to supply a pulse to the sampling valve 54 so that a sample is taken every 90 seconds during the process.

The carrier pump 14 may be set to provide a carrier fluid flow rate of about 1.00 mL/min at a pressure of 500 p.s.i.g. The carrier fluid may be maintained at a temperature of between about 25° to about 45° C.

The detector 16 may be a MIRAN-LA infrared analyzer having a pre-set slit width of 2 millimeters. The analytical wavelength may be 5.90 microns. The detector output scale may be 0–0.25 and the detector meter response 1.

The present invention is applicable to the analysis of any infrared absorbing material dissolved into an organic solvent or mixture which does not absorb light at the same frequency as the material being analyzed. The present invention is specifically applicable to high concentration analysis (for example concentrations of 1–100%) which otherwise could not be accomplished by light transmission methods because of the non-linearity of the measurement when concentrations are over a few percent and therefore would require expensive instrumentation such as FTIR with an ATR cell. However, even the FTIR method with the ATR cell can not be used with some chemical processes because many polymerization reactions will result in the coating of the cell, while the present invention is capable of providing a highly accurate analysis in those cases. The flow injection analysis according to the present invention permits the high concentration analysis because of the sample dilution capabilities.

As described above, the method and analyzer of the present invention will provide an indication of the rate of reaction taking place in a chemical process. In processes wherein the reaction is initiated and sustained by the addition of a catalyst and stopped by the addition of a quenching agent, having an indication of the rate and progress of the reaction at frequent intervals will provide a basis for increasing or decreasing the addition of the catalyst. Also, by sounding an alarm or providing some other type of warning just prior to the desired endpoint of the reaction, a quenching agent may be added to the reaction at the proper time or other steps taken to halt the reaction.

While the invention has been described above with reference to a specific embodiment thereof, it is apparent that many changes, modifications, and variations can be made without departing from the concept disclosed herein. Accordingly, it is intended to embrace all such changes, modifications, and variations that fall within the scope of the appended claims.

What is claimed is:

1. An analyzer for monitoring a chemical reaction in a chemical process comprising:

a. a sample gatherer for gathering a sample of a reaction mixture of the chemical process;

b. a source of a dry organic liquid carrier, containing a quenching agent, to provide a flow stream thereof;

c. an injector for injecting the sample into a flow stream of said dry organic liquid carrier;

d. an infrared detector for detecting an amount of a particular species of the reaction mixture in the sample which is indicative of the progress of the chemical process, and e. means for passing said flow stream of dry organic liquid carrier with said sample through said infrared detector.

2. An analyzer for monitoring a chemical reaction in a chemical process comprising:

a. a sample gatherer for gathering a sample of a reaction mixture of the chemical process;

b. a source of a dry organic liquid carrier, containing a quenching agent, to provide a flow stream thereof;

c. an injector for injecting the sample into a flow stream of said dry organic liquid carrier;

d. an infrared detector for detecting an amount of a particular species of the reaction mixture in the sample which is indicative of the progress of the chemical process, and e. means for passing said flow stream of dry organic liquid carrier with said sample through said infrared detector, wherein said sample gatherer and said injector include means for periodically gathering and injecting a plurality of samples during the chemical process and passing said flow stream with each said sample through said detector.

3. The analyzer of claim 2 wherein said gathering means and said injecting means includes a chamber of fixed volume, and means for moving said chamber between a first position wherein the reaction mixture flows into said chamber and a second position wherein the chamber is positioned in the flow stream of the liquid carrier so that the fixed volume of the reaction mixture in said chamber is entrained in said flow stream.

4. The analyzer of claim 2 wherein said gathering means and said injection means includes a sampling valve moveable between a first position and a second position, said valve including a first and second set of inlet and outlet ports and a sample gathering orifice, said orifice of said valve being positioned in the first position of the valve to provide communication between the inlet and outlet ports of said first set and being positioned in said second position of said valve to provide communication between the inlet and outlet ports of said second set, and further including means connecting the flow stream to said first set of ports to provide a supply of the reaction mixture from the flow stream to said valve and through said orifice, and means connecting the source of dry organic liquid carrier to the inlet port of said second set and connecting the outlet port of said second set to said analyzer.

5. The analyzer of claim 4 wherein said orifice is of a fixed predetermined volume.

6. The analyzer of claim 4 further including means for controlling the rate of flow of said carrier fluid to said sampling valve.

7. The analyzer of claim 6 wherein said means for controlling the rate of flow of said carrier fluid is an isocratic pump.

8. The analyzer of claim 4 further including means for causing the flow of a standard solution of the reaction mixture having a known amount of the species to be detected therein to the inlet port of said first set and through said sampling orifice while cutting off the flow of the reaction mixture from the chemical process to the sampling valve.

9. An analyzer for monitoring a chemical reaction in a chemical process comprising:

a. a circulating line for circulating a portion of the reaction mixture of the chemical process from the chemical process through a sample infeed line and back to the process;

b. a diverter for diverting a portion of the reaction mixture portion being recirculated from the sample infeed line to a sample gatherer;

c. a sample gatherer for gathering a fixed volume of sample of the reaction mixture of the chemical process;

d. an injector for periodically injecting the fixed volume of sample into a flow stream of an organic liquid carrier;

e. an infrared detector for detecting an amount of a particular species of the reaction mixture in the sample which is indicative of the progress of the chemical process, and f. means for passing said flow stream of said organic liquid carrier, containing a quenching agent, with the fixed volume of sample through said infrared detector.

* * * * *